US006835806B2

(12) United States Patent
Chang

(10) Patent No.: US 6,835,806 B2
(45) Date of Patent: Dec. 28, 2004

(54) CELL GROWTH REGULATION SYSTEM

(75) Inventor: Jaw-Kang Chang, San Carlos, CA (US)

(73) Assignee: Phoenix Pharmaceuticals, Inc., Belmont, CA (US)

( * ) Notice: Subject to any disclaimer, the term of this patent is extended or adjusted under 35 U.S.C. 154(b) by 333 days.

(21) Appl. No.: 09/822,540

(22) Filed: Mar. 30, 2001

(65) Prior Publication Data

US 2002/0058620 A1 May 16, 2002

Related U.S. Application Data

(60) Provisional application No. 60/194,561, filed on Apr. 3, 2000.

(51) Int. Cl.[7] .............................................. A61K 38/00
(52) U.S. Cl. ............................ 530/300; 530/324; 514/2
(58) Field of Search ................................ 530/328, 300, 530/324; 435/69.1; 514/2

(56) References Cited

U.S. PATENT DOCUMENTS 5,854,205 A * 12/1998 O'Reilly et al. ................ 514/2
6,201,104 B1 * 3/2001 MacDonald et al. ........ 530/327

OTHER PUBLICATIONS

Heidtmann et al. British Journal of Cancer (Dec. 1999) vol. 81, No. 8, pp. 1269–1273.*

* cited by examiner

Primary Examiner—Laurie Scheiner
(74) Attorney, Agent, or Firm—CR Miles, P.C.; Craig Miles

(57) ABSTRACT

Stable water soluble polypeptides which are potent inhibitors of endothelial cell proliferation and of angiogenesis. Polypeptide inhibitors of endothelial cell growth may have important uses in the elucidation of the mechanism of angiogenesis, disease diagnosis and prognostication, and drug therapies for use in animals and humans.

3 Claims, 10 Drawing Sheets

JCK-362(Endostatin 52-114)-NH$_2$ (Human) (63 Amino Acids)

ADRAAVPIVNLKDELLFPSWEALFSGSEGPLKPGARIFSFDGKDVLRHPT
WPQKSVWHGSDPN-NH$_2$

FIG. 1

JKC-367 (Endostatin 84-114)-NH₂ (Human) (31 Amino Acids)

PGARIFSFDGKDVLRHPTWPQKSVWHGSDPN-NH₂

FIG. 2

JKC-367 (Endostatin 84-114)-NH$_2$ (Human) 31 Amino Acids

PGARIFSFDGKDVLRHPTWPQKSVWHGSDPN-NH$_2$

GARIFSFDGKDVLRHPTWPQKSVWHGSDPN-NH$_2$
ARIFSFDGKDVLRHPTWPQKSVWHGSDPN-NH$_2$
RIFSFDGKDVLRHPTWPQKSVWHGSDPN-NH$_2$
IFSFDGKDVLRHPTWPQKSVWHGSDPN-NH$_2$
FSFDGKDVLRHPTWPQKSVWHGSDPN-NH$_2$
SFDGKDVLRHPTWPQKSVWHGSDPN-NH$_2$
FDGKDVLRHPTWPQKSVWHGSDPN-NH$_2$
DGKDVLRHPTWPQKSVWHGSDPN-NH$_2$
GKDVLRHPTWPQKSVWHGSDPN-NH$_2$
KDVLRHPTWPQKSVWHGSDPN-NH$_2$
DVLRHPTWPQKSVWHGSDPN-NH$_2$
VLRHPTWPQKSVWHGSDPN-NH$_2$
LRHPTWPQKSVWHGSDPN-NH$_2$
RHPTWPQKSVWHGSDPN-NH$_2$
HPTWPQKSVWHGSDPN-NH$_2$
PTWPQKSVWHGSDPN-NH$_2$
TWPQKSVWHGSDPN-NH$_2$
WPQKSVWHGSDPN-NH$_2$
PQKSVWHGSDPN-NH$_2$
QKSVWHGSDPN-NH$_2$
KSVWHGSDPN-NH$_2$
SVWHGSDPN-NH$_2$
VWHGSDPN-NH$_2$

FIG. 3

JKC-367 (Endostatin 84-114)-NH₂ (Human) 31 Amino Acids)
PGARIFSFDGKDVLRHPTWPQKSVWHGSDPN-NH₂

PGARIFSFDGKDVLRHPTWPQKSVWHGSDP-NH₂
PGARIFSFDGKDVLRHPTWPQKSVWHGSD-NH₂
PGARIFSFDGKDVLRHPTWPQKSVWHGS-NH₂
PGARIFSFDGKDVLRHPTWPQKSVWHG-NH₂
PGARIFSFDGKDVLRHPTWPQKSVWH-NH₂
PGARIFSFDGKDVLRHPTWPQKSVW-NH₂
PGARIFSFDGKDVLRHPTWPQKSV-NH₂
PGARIFSFDGKDVLRHPTWPQKS-NH₂
PGARIFSFDGKDVLRHPTWPQK-NH₂
PGARIFSFDGKDVLRHPTWPQ-NH₂
PGARIFSFDGKDVLRHPTWP-NH₂
PGARIFSFDGKDVLRHPTW-NH₂
PGARIFSFDGKDVLRHPT-NH₂
PGARIFSFDGKDVLRHP-NH₂
PGARIFSFDGKDVLRH-NH₂
PGARIFSFDGKDVLR-NH₂
PGARIFSFDGKDVL-NH₂
PGARIFSFDGKDV-NH₂
PGARIFSFDGKD-NH₂
PGARIFSFDGK-NH₂
PGARIFSFDG-NH₂
PGARIFSFD-NH₂
PGARIFSF-NH₂

FIG. 4

VALNSPLSGGMRGIRGADFQCFQQARAVGLAGTFRAFLSSRLQDLY
49 50  52                                                            84
SIVRRADRAAVPIVNLKDELLFPSWEALFSGSEGPLKPGARIFSFDGK
       100                              114          118
DVLRHPTWPQKSVWHGSDPNGRRLTESYCETWRTEAPSATGQASSL

LGGRLLGQSAASCHHAYTVLCIENSFMTAS

FIG. 5

SEQUENCE LISTING

<160> NUMBER OF SEQ ID NOS: 2

<210> SEQ ID NO 1
<211> LENGTH: 63
<212> TYPE: PRT
<213> ORGANISM: Homo sapiens

<400> SEQUENCE: 1

Ala Asp Arg Ala Ala Val Pro Ile Val Asn Leu Lys Asp Glu Leu Leu
1               5                   10                  15

Phe Pro Ser Trp Glu Ala Leu Phe Ser Gly Ser Glu Gly Pro Leu Lys
            20                  25                  30

-continued

```
Pro Gly Ala Arg Ile Phe Ser Phe Asp Gly Lys Asp Val Leu Arg His
            35                  40                  45

Pro Thr Trp Pro Gln Lys Ser Val Trp His Gly Ser Asp Pro Asn
    50                  55                  60

<210> SEQ ID NO 2
<211> LENGTH: 31
<212> TYPE: PRT
<213> ORGANISM: Homo sapiens

<400> SEQUENCE: 2

Pro Gly Ala Arg Ile Phe Ser Phe Asp Gly Lys Asp Val Leu Arg His
1               5                  10                  15

Pro Thr Trp Pro Gln Lys Ser Val Trp His Gly Ser Asp Pro Asn
            20                  25                  30
```

CELL GROWTH REGULATION SYSTEM

This application claims the benefit of United States Provisional Patent Application No. 60/194,561, filed Apr. 3, 2000.

BACKGROUND

Generally, stable water soluble purified polypeptides which are potent inhibitors of endothelial cell proliferation in-vivo may be useful in elucidating the mechanism by which angiogenesis is regulated. Specifically, stable water soluble polypeptide inhibitors of angiogenesis reduce the volume of animal tumors, including human tumors, in-vivo.

Evidence suggests that angiogenesis is essential for the growth and persistence of solid tumors. Folkman, 1989; Hori et al., 1991; Kim et al. 1993. To stimulate angiogenesis, tumors up regulate their production of a variety of angiogenic factors, including the fibroblast growth factors. Kandel et al., 1991. Studies suggest that proteins such as murine endostatin protein (184 residue protein derived from the cleavage of Type XVIII collagen expressed by hemanioendothelioma EOMA or obtained as an expression product from recombinant cells) may cause marked reduction of mouse tumors. U.S. Pat. No. 5,854,205, hereby incorporated by reference. Similarly, angiostatin protein (200 residue protein derived from the cleavage of plasminogen) has been shown to inhibit the metastasis of certain primary mouse tumors. http://www.ultranet.com/jkimball/BiologicalPages/A/Angiogenesis.html (Mar. 31, 2000), hereby incorporated by reference.

The potential use of the entire endostatin and angiostatin proteins as human drug therapies has been surrounded by enormous publicity and there appears to be a large commercial market for endostatin or angiostatin proteins, or other angiogenesis inhibitors as drugs. Because of the growing commercial, therapeutic, and research potential for angiogenesis inhibitors, numerous research studies have been conducted which disclose a variety of uses for the endostatin and angiostatin proteins. In spite of the numerous studies conducted with whole endostatin and angiostatin proteins, substantial problems remain unresolved with regard to providing angiogenesis inhibitors that can be commercialized, or used as drug therapies in animals or in humans, or as angiogenic compounds in research.

A significant problem with whole protein angiogenesis inhibitors, for example endostatin proteins or angiostatin proteins, can be that it may be difficult to predict what portion of the protein is biologically active. As disclosed by U.S. Pat. No. 5,854,205, hereby incorporated by reference, the endostatin protein is comprised of 184 residues with a molecular weight of about 20 kDa. Similarly, the angiostatin protein comprised of 200 residues has a molecular weight of about 21 kDa. With respect to such protein angiogenesis inhibitors, it is difficult to predict which residues encompassed by the primary structure of the protein may be responsible for the observed angiogenesis inhibition activity. One aspect of this difficulty may be that the biologically active portion of the protein may comprise discontinuous regions of the primary structure of the protein which must be held in a specific secondary or tertiary structure by the remaining portions of the protein molecule to acquire angiogenesis inhibition activity. A second aspect of this difficulty may be that the biologically active region of the protein molecule may be a continuous region of the primary structure of the protein which must be similarly held in a specific secondary or tertiary structure by the remaining portion of the protein molecule to acquire angiogenesis inhibition activity. A third aspect of this difficulty may be that there may be a plurality of biologically active regions encompassed by the primary sequence of the protein some of which may be discontinuous or some of which may be continuous. A fourth aspect of this difficulty may be that such plurality of biologically active regions encompassed by the primary sequence of the protein overlap one another and may not be independently excised from the primary sequence with out disabling the other biologically active regions. A fifth aspect of this difficulty may be that the region of a protein having angiogenesis inhibition activity may be discontinuous from the region of the protein which has an affinity for the target cell receptor. A sixth aspect of this difficulty may be that a portion of an angiogenic protein may apparently lack biological activity when assayed in-vitro but may acquire biological activity when assayed in-vivo. A seventh aspect of this difficulty may be that a portion of an angiogenic protein when chemically or enzymatically excised, or when identified and subsequently chemically synthesized, may not be biologically available to the target receptor in-vitro or in-vivo. This lack of biological availability may be due to insolubility of the compound, a binding affinity to surrounding substrates that is greater than to the target cell receptor, instability of the angiogenic compound with respect to cleavage, or with respect to modification of the peptide backbone, N-terminus, C-terminus, side chain, or other peptide or chemical moiety associated with the excised or chemically synthesized portion of the protein. Due to these, and a variety of other difficulties well known to those with skill in the art, assignment of angiogenesis inhibition activity to any specific biochemical structure, which may be a portion of a protein, such as endostatin or angiostatin, or any other molecule, may be unpredictable without an actual reduction to practice involving at least isolation, purification, and in-vitro and in-vivo assays to confirm biological activity of a particular compound. Subsequent characterization and identification of the chemical structure may further serve to differentiate biologically active compounds which in every other respect may seem similar.

Another significant problem with the commercial development of additional novel angiogenesis inhibitors may be that small polypeptides (primary sequences comprised of 65 or fewer amino acid residues) have not been shown to have angiogenesis inhibition activity. One aspect of this problem may be due to the failure to incorporate within the primary sequence of the polypeptide the essential residues which have an affinity for the target cell receptor. A second aspect of this problem may be the failure to incorporate within the primary sequence of the polypeptide the essential residues which comprise the region conferring angiogenesis inhibition activity to the polypeptide. A third aspect of this problem may be that in-vitro methods of assaying polypeptides for biological activity may fail to properly address the processing requirements of the polypeptide in a manner which in-vivo methods for assaying polypeptides do address.

Another significant difficulty with existing angiogenesis inhibitors may be that therapeutic results are difficult to replicate. With respect to endostatin protein, for example, it can be difficult to reproduce results which show endostatin protein dramatically shrinks tumors. Harvard Cancer Research Questioned, New York Times Company, Associated Press (1998); Ovarian Cancer Research Notebook http://www.slip.net/mcdavis/database/angio188.htm; National Cancer Institute Clarifies Role in Development of Endostatin, *Angiogenesis Weekly*, (Tuesday, Oct. 5, 1999), each hereby incorporated by reference.

Another significant problem with existing angiogenesis inhibitors may be stability. Some angiogenesis inhibitors have proven to be unstable in shipment, or during subsequent routine handling, or during routine use in research studies resulting in a partial or complete loss of biological activity. National Cancer Institute Clarifies Role in Development of Endostatin, *Angiogenesis Weekly,* (Tuesday, Oct. 5, 1999), hereby incorporated by reference.

Another significant problem with existing angiogenesis inhibitors may be that it is difficult to produce sufficient amounts for wide spread use either for research or for therapies. Recombinant unfolded liner endostatin protein, for example, is insoluble (as disclosed by U.S. Pat. No. 5,854,205, hereby incorporated by reference) and may be difficult to use in applications which require soluble protein or soluble portions thereof, such as isotopic labeling, affinity purification substrates for receptor proteins, competing other polypeptides or proteins in solution, for use in diagnostic kits for detecting the presence of antibodies, or for use as conventional drug therapies in animals or humans. The difficulty in producing large quantities of some types of angiogenesis inhibitors, including protein angiogenesis inhibitors, may present significant obstacles in developing vascularization inhibition therapy models.

Another significant problem with existing angiogenesis inhibitors may be that the effective dosages are too high. For example, the amount of angiostatin protein used in animal studies has been criticized as being too high for clinical trials in humans. Annual Review of Medicine, 49: 407–424, (1998); and http://www.lef.org/protocols/abstracts/cancertreat-abstr.html, each hereby incorporated by reference. One aspect of high dosages with respect to conventional protein angiogenic inhibitors may be that a substantial portion of the protein by weight does not contribute to the observed angiogenic inhibition activity. A second aspect of high dosages with respect to conventional protein angiogenic inhibitors may be that the angiogenic inhibition activity on a molar basis may be lower than is practical for a particular application. A third aspect of high dosages with respect to conventional protein angiogenic inhibitors may be that the protein angiogenic inhibitors are unstable with respect to proteolytic activity, temperature, handling, or methods of in-vitro or in-vivo assays, or may have other attributes such as insolubility, a processing requirement, or high elimination rates in-vivo, as examples, which may render the active portions of conventional angiogenic inhibitors biologically unavailable or at levels which are not practical for applications such as human drug therapy.

Another significant problem with existing angiogenesis inhibitors may be that they are not suitable for use in humans. One aspect of this problem can be that such angiogenesis inhibitors comprise proteins derived from species other than human. For example murine endostatin (derived from mouse tissue, mouse cell lines, or recombinant expression of mouse endostatin genes) which has shown to be effective in regulating endothelial cell growth in mice or effective in reducing the volume of mouse tumors may not be applicable to the regulation of endothelial cell growth in humans or for the reduction in volume of human tumors grown in mouse or for the reduction of tumor volume in humans. See for example, U.S. Pat. No. 5,854,205, hereby incorporated by reference.

Another significant problem with existing angiogenesis inhibitors may be solubility. One aspect of this problem may be that angiogenic inhibitor proteins become denatured during isolation or purification and may subsequently become insoluble as such proteins unfold presenting additional hydrophobic core residues. As disclosed by U.S. Pat. No. 5,854,205, hereby incorporated by reference, unfolded recombinant mouse endostatin is not soluble and may not be tested in-vitro. A second aspect of this problem may be that only a small percentage of the unfolded protein may spontaneously refold, and an even smaller percentage of the protein molecules may refold properly. Unfolded or improperly folded molecules may have no or lower biological activity on a weight or molar basis than the properly folded proteins. A third aspect of this problem may be that unfolded insoluble angiogenic proteins may have to be injected as a suspension of particulate. This may make the preparation of the appropriate dosage more difficult or more time consuming. Moreover, reabsorption of injected precipitates may be variable from individual to individual or injection site to injection site. It is well known to those with skill in the art that injecting insoluble suspensions of proteins, peptides, or protein-peptide conjugates into animals often stimulates the production of antibodies to such insoluble particulate, however, the results of immunization of animals with such insoluble particulate may not be predictable even when using what appears to be the same amount of suspended particulate.

Another problem with generating additional novel angiogenesis inhibitors may be that compounds which may fail to show inhibition of angiogenic activity in-vitro may show unexpectedly high levels of angiogenic inhibition activity in-vivo. This discovery teaches away from conventional wisdom of those skilled in the art. Up until the present invention it was thought that "proteins or peptides derived from . . . sources including manual or automated synthesis, may be quickly and easily tested for endothelial proliferation inhibiting activity using a biological assay such as the bovine capillary endothelial cell proliferation assay." See U.S. Pat. No. 5,854,205, hereby incorporated by reference. However, it is now understood that stable water soluble polypeptides may show no effect in-vitro but still retain the ability to reduce the volume of established xenographs in-vivo. J. D. Hunt et al., *Internal Peptides Within Endostatin Lacking Zinc-Binding Domains Inhibit Angiogenesis,* Publishing ID: 3106, Meeting of the American Cancer Society (Apr. 4, 2000), hereby incorporated by reference. As generally mentioned above, and specifically with respect to endostatin protein, it is unpredictable and difficult to assess which portions of a protein may encompass observed biologically active. Moreover, minor chemical modifications, such as the reduction in the number of residues, or the amidation of the C-terminus of a polypeptide, for example, may confer unexpected properties upon a polypeptide such as increased biological activity, increased stability, or increased solubility. As such, no change in the structure of a protein or of a polypeptide or other compound, regardless as to how minor it may be perceived before hand, should be considered silent until proven so by the appropriate testing in-vitro and in-vivo as disclosed below.

Another problem with generating additional novel angiogenesis inhibitors may be that the molecular structure may not be chemically synthesized in substantial quantity. Angiogenesis inhibiting proteins such as endostatin (184 residues) and angiostatin (200) may not be able to be chemically synthesized with any substantial success. Conventional methods of chemical synthesis resulting in substantial quantities of purified peptide (over 10 milligrams) are typically limited to peptide sequences having fewer than 70 residues. Peptides which have fewer than 35 residues may be candidates for the chemical synthesis of large amounts of synthetic purified peptide in the kilogram quantities. Peptides and proteins have a greater number of residues, are generally produced by recombinant technologies. Although shorter polypeptides may also be produced by recombinant technology, chemical synthesis of shorter polypeptides may be less expensive, less time consuming, and result in a more highly purified end product. Moreover, conventional methods of chemical synthesis of polypeptides are available (either in-house or commercially) to a broader range of companies and research individuals than recombinant techniques.

Another problem with generating additional novel angiogenesis inhibitors may be that both the human and mouse counterparts of the same angiogenic inhibitor may not be available. Having both the mouse and human counter parts of the same angiogenic inhibitor allows for a animal model in which angiogenic inhibitors may be researched and the findings more readily extrapolated to similar experimental trials with humans.

With respect to making and using cell growth regulators, and specifically with respect to angiogenic inhibitors the present invention discloses compositions and technology which address every one of the above-mentioned problems in a practical fashion.

SUMMARY OR THE INVENTION

A broad object of embodiments of the invention can be to provide potent polypeptide inhibitors of angiogenesis and methods for their use. Polypeptide inhibitors of angiogenesis may be important in elucidating the process of vascularization which involves both positive and negative regulators. Vascularization which is induced by pro-angiogenic factors may be balanced using various embodiments of the invention which may include negative regulators of angiogenesis.

Another broad object of embodiments of the invention can be to provide polypeptide inhibitors of angiogenesis that can be labeled isotopically, or with other molecules, or with other proteins for use in the detection and visualization of binding sites for negative regulation of angiogenesis with state of the art techniques such as positron emission tomography, autoradiography, flow cytometry, radioreceptor binding assays, competition assays, immunochemistry, or the like.

Another significant object of an embodiment of the invention can be to provide polypeptide inhibitors of angiogenesis which may be used to identify, isolate, or purify receptor proteins which bind to such polypeptide inhibitors along with the methods for reversibly associating the receptor proteins with the polypeptide invention. These receptor proteins may include the human receptor protein which binds the human endostatin protein.

Another significant object of an embodiment the invention can be to provide polypeptide inhibitors of angiogenesis which may be used to produce monoclonal or polyclonal antibodies which have an affinity to such polypeptide inhibitors or to the endostatin protein or portions thereof.

Another object of an embodiment of the invention can be to provide polypeptide inhibitors of angiogenesis which may be used as agonists or antagonists of the endostatin protein or a portion of the endostatin protein.

Another object of an embodiment of the invention can be to provide polypeptide inhibitors of angiogenesis for use in diagnostic or prognostic methods or kits for detecting the presence and quantity of antibodies which bind endostatin protein or a portion thereof in biological fluids. Kits and the methods for detecting such antibodies can be in various configurations well known to those of ordinary skill in the art. One aspect of this embodiment of the invention may be to provide a method for the detection of or prognosis of cancer.

Another significant object of an embodiment of the invention can be to provide polypeptide inhibitors of angiogenesis as a therapy for treating diseases and processes that are mediated by angiogenesis. Such diseases and processes, may for example include, but are not limited to, preventing tumor growth, inhibiting tumor growth, reduction in tumor volume, elimination of tumors, inhibiting metastasis, preventing metastasis, inducing dormancy of tumors and metastasis, preventing arteriosclerosis, inhibiting atherosclerosis, reducing existing plaque in blood vessels, reducing intimal plaque neovascularization, hemangioma, solid tumors, leukemia, myocardial angiogenesis, neovascular glaucoma, diabetic retinopathy, retrolental fibroplasia, arthritis, diabetic neovascularizaton, macular degeneration, wound healing, peptic ulcer, fractures, keloids, hematopoiesis, ovulation, menstruation, or placentation.

Another object of an embodiment of the invention can be to provide polypeptide inhibitors of angiogenesis for in-vivo use without acquired drug resistance.

Another object of an embodiment of the invention can be to provide polypeptide inhibitors of angiogenesis for in-vivo use which produce minimal side effects.

Another object of an embodiment of the invention can be to provide polypeptide inhibitors which require in-vivo processing to acquire cell growth regulation activity.

Yet another object of an embodiment of the invention may be to provide polypeptides which may be used to detect and quantify endostatin biosynthesis.

Still another significant object of an embodiment of the invention can be can be to provide polypeptide inhibitors of angiogenesis for delivering cytotoxic molecules to receptor targets for therapeutic or research purposes.

Another object of an embodiment of the invention is to provide a composition comprising antibodies. One aspect of this objective may be to provide either monoclonal, or polyclonal, or mixtures thereof, to polypeptide inhibitors of angiogenesis, or to corresponding regions of the endostatin protein. A second aspect of this objective may be to provide either monoclonal, or polyclonal, or mixtures thereof which inhibit binding of such monoclonal, or polyclonal antibodies to polypeptide inhibitors of angiogenesis.

Another significant object of an embodiment of the invention can be can be to provide polypeptide inhibitors of angiogenesis which can be synthesized chemically which may obviate the use of enzymatic cleavage of endostatin-protein or the products of recombinant technologies for production of such polypeptide angiogenesis inhibitors.

Another object of an embodiment of the invention can be to provide polypeptides which bind to receptor proteins which are associated with regulation of angiogenesis, but other than competing with other polypeptides or proteins for the same receptor binding site, do not directly regulate cell growth. One aspect of this object may be to provide polypeptides which comprise only a binding region to compete other molecules which bind to the same receptor site. A second aspect of this object may be to provide polypeptides that have a binding region and a cell growth regulation region. With regard to this second aspect, the cell growth regulation region may be inactive in-vitro but active in-vivo, or may be active in-vitro but inactive in-vivo, or may be active in-vitro and active in-vivo.

Another object of an embodiment of the invention can be to provide polypeptide angiogenesis inhibitors which regulate the growth endothelial cells in-vivo at low dosages. One aspect of this object of the invention may be to use smaller amounts of such polypeptide by weight or by moles than the amount of endostatin protein used by weight or by moles with similar or enhanced therapeutic results in treatment of the same disease.

Another object of an embodiment of the invention can be to provide polypeptides which inhibit the growth of human prostrate cancer tumors or cells in-vivo.

Another object of an embodiment of the invention can be to provide polypeptide inhibitors of angiogenesis which may be stable in aqueous solutions or water.

Another object of an embodiment of the invention can be to provide polypeptide inhibitors of angiogenesis which correspond to a portion of the human endostatin protein. One aspect of this object is to provide such polypeptides which are not the N-terminal portion of the endostatin protein. A second aspect of this object may be to provide such human polypeptide from the internal region of the human endostatin protein.

Another object of an embodiment of the invention can be to provide polypeptide inhibitors of angiogenesis which correspond to a portion of the mouse endostatin protein. An aspect of this object is to provide such mouse polypeptide from the internal region of mouse endostatin protein. A second aspect of this object is to provide such mouse polypeptides which correspond to similar regions of the human endostatin molecule.

Another object of an embodiment of the invention can be to provide methods of enzymatic cleavage of human and mouse endostatin which generate polypeptides which inhibit angiogenesis.

Another object of an embodiment of the invention can be to provide a stable, water soluble, 63-residue polypeptide inhibitor of angiogenesis.

Another object of an embodiment of the invention can be to provide a stable, water soluble, 31-residue poly peptide inhibitor of angiogenesis.

Another object of an embodiment of the invention can be to provide methods of chemical synthesis of a nested set of polypeptides or analogs from an internal regions of the human or mouse endostatin protein.

These and other independent objects, features, and advantages of the invention are disclosed throughout other areas of the specification.

BRIEF DESCRIPTION OF THE DRAWINGS

FIG. 1 shows the primary sequence of the polypeptide JCK-362.

FIG. 2 shows the primary sequence of the polypeptide JCK-367.

FIG. 3 shows the primary sequence of N-terminal truncations to the polypeptide JCK-367.

FIG. 4 shows the primary sequence of C-terminal truncations to the polypeptide JCK-367.

FIG. 5 shows the primary sequence of the endostatin protein.

DETAILED DESCRIPTION OF THE PREFERRED EMBODIMENTS

Figure 6:
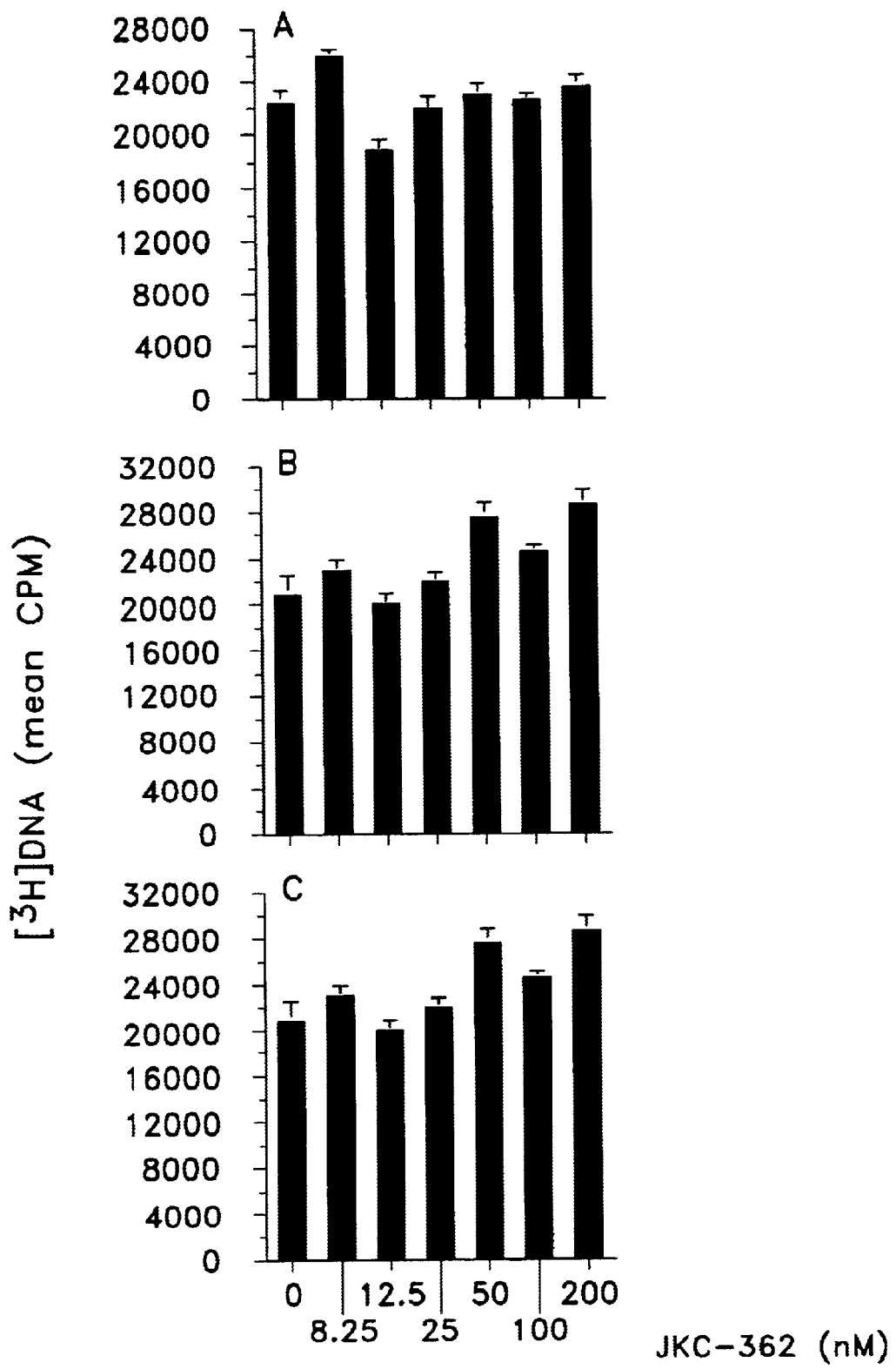
FIG. 6 shows the uptake of tritium labeled DNA into PC-3 cells, human lung adenocarcinoma 201T cells, and human umbilical vein endothelial cells.

As can be easily understood from the foregoing, the basic concepts of the present invention may be embodied in a variety of ways. It involves methods of producing angiogenesis inhibitors, polypeptide angiogenesis inhibitors, and methods of using such polypeptide angiogenesis inhibitors to regulate cell growth. In this application, the cell regulation techniques are disclosed as part of the results shown to be achieved by the various polypeptide angiogenesis inhibitors described and as steps which are inherent to utilization. They are simply the natural result of utilizing the angiogenesis inhibitors as intended and described. In addition, while some angiogenesis inhibitors are disclosed, it should be understood that these not only accomplish certain methods but also can be varied in a number of ways. Moreover, the present invention includes a variety of aspects which may be selected independently or in different combinations based upon the particular application or need to be addressed. Importantly, as to all of the foregoing, all of these facets should be understood to be encompassed by this disclosure.

Stable water soluble polypeptides having potent antitumor activity in-vivo are disclosed. As shown by FIG. 1, the first polypeptide comprising 63-residues and a molecular weight of about 6985 (JKC-362 or '362 peptide) reduces the volume of established xenografts in nude mice. As shown by FIG. 2, the second polypeptide comprising 31 residues encompasses a portion of the primary sequence internal to the '362 peptide having a molecular weight of about 3533 (JKC-367 or '367 peptide) inhibits the expansion of human tumor xenografts. Both the '362 peptide and the '367 peptide have similar antiangiogenic or anticancer properties, or can further be used in research for the elucidation of the mechanism by which whole proteins such as endostatin inhibit angiogenesis.

Residues 52–114 which comprise the '362 peptide were selected for chemical synthesis based upon modeling the potential proteolytic cleavage sites within the primary sequence of the human endostatin protein. The '362 peptide was selected based upon the expectation that the endostatin protein may be processed in-vivo at the dibasic residue pair Arg-Arg (residues 50 and 51) and the triplet Gly-Arg-Arg (residues 115–117) which upon proteolytic cleavage would generate the C-terminal amide '362 peptide. Peptide '367 was similarly modeled based upon the expectation that the '362 peptide would be processed further at the internal Lys residue (residue 83) which upon proteolytic cleavage would generate the '362 peptide and the remaining portion of the '367 peptide. As such, the development of the '362 and the '367 peptides as angiogenesis inhibitors occurred entirely independent of, and in an entirely different manner than the development process of the endostation protein angiogenesis inhibitors disclosed to date.

Once the primary sequence for the '362 and the '367 peptide were determined by modeling, each was synthesized chemically using fluorenyloxymethylcarbonyl (FMOC) amino acids or tertbutyloxymethylcarbonyl (BOC) amino acids either with an automated peptide synthesizer, or manually as is understood by techniques well know to those skilled in the art. See also Solid Phase Peptide Synthesis: A practical approach, E. Atherton and R. C. Sheppard, IRL Press, Oxford, England, hereby incorporated by reference.

The resulting mixture of polypeptides from the chemical synthesis were separated from one another by reverse phase HPLC using columns packed with silica having a pore of between 80 Å and 300 Å and a C-4, C-8, or C-18 ligand attached. The columns were equilibrated with 0.1% trifluoroacetic acid in water at a flow rate dependent on column size as would be understood by those having skill in the art. The synthetic peptide mixtures were applied to the reverse phase HPLC columns and eluted with 0.1% trifluoroacetic acid in acetonitrile using a gradient of 0% to about 80% over a period of about 1 hour. Fractions were collected at about 0.5 minute intervals. Fractions were subsequently analyzed for homogeneity by re-application and elution from the reverse phase HPLC system, mass spectrometry, SDS-PAGE, or automated Edman degradation on a Perkin Elmer/Applied Biosystems Model 470A protein sequencer. As described by Perkin Elmer/Applied Biosystems, Inc., Foster City, Calif. The homogeneous products were subsequently assayed as described below.

The invention also encompasses polypeptides which have substantially similar amino acid sequence and which are capable of inhibiting proliferation of endothelial cells, or reducing the volume of murine or human tumors in-vitro or in-vivo, and also includes substantially similar primary sequences which are capable of targeting and binding the endostatin receptor, or other angiogenesis related receptors. For example, silent substitutions of residues wherein the replacement of the residue with structurally or chemically similar residue(s) does not significantly alter the structure, conformation, or activity of the polypeptide. Such silent substitutions are intended to fall within the scope of the claims of this application along with purified polypeptides related to the '362 or '367 wherein one or more residues is removed from either end or both ends, or from an internal region of the protein, or wherein one or more residues is added to either end or both ends, or to an internal location in either peptide. Moreover, purfied polypeptides having chemical moieties or residues added for chemical or radiolabeling, such as, an added tyrosine for $^{125}$iodine labeling are also understood to be encompassed by the invention. Similarly, the N-terminus in some embodiments of these purified polypeptide inventions were prepared as amino, acetyl, formyl, or left with a residual FMOC or BOC group intact. In certain embodiments, the C-terminus was left bound to the resin, or cleaved to yield various C-terminal moieties, such as carboxyl or amide by choice of the corresponding BHA, PAM, or amide solid phase resin. See also, FIG. 1 Research Plan, Phoenix Pharmaceuticals which is hereby incorporated by reference.

Similarly, the corresponding sequences to the '362 peptide and the '367 peptide in the murine system have been modeled as above described and analogs as above described for the corresponding murine '362 peptide and the '367 peptide are included within this application. As to both the human and the murine polypeptides, a nested set of peptides has been prepared as exemplified by FIGS. 3, 4 and 5 which disclose truncated forms of the human '362 peptide.

Importantly, the endostatin protein (shown by FIG. 5) has a primary structure with a molecular weight of about 20 kDA and contains a zinc-binding domain which is critical in maintaining the protein's function as an inhibitor of endothelial cell growth. Neither the '367 peptide or the '362 peptide contain this essential zinc-binding domain and, yet unexpectedly, maintain the ability to inhibit the growth of or reduce the volume of human tumors in-vivo. The use of the '362 peptide or the '367 peptide, having the primary sequences disclosed by FIGS. 1 and 2, to inhibit or reduce human tumor volumes may be the first demonstration of a biological response to polypeptides corresponding to an internal region of the primary structure of the human endostatin protein ('362 peptide amide corresponds to residues 62–126 of human endostatin protein).

The response to the '362 peptide and the '367 peptide is further differentiated from the endostatin protein in that neither polypeptide exhibits endothelial growth inhibition in-vitro. To determine if the '362 peptide or the '367 peptide affects the in-vitro growth of cells, the '362 peptide was tested in culture dishes for the ability to inhibit the growth of prostrate tumor cells or of lung tumor cells. Radioactive hydrogen ($^3$ H) was attached to thymidine([$^3$H]hymidine), which is one of the components of DNA. Cells that grow in the presence of [$^3$H]thymidine incorporate the radioactive thymidine into their DNA. Cells which are not growing do not incorporate the [$^3$H] thymidine into their DNA.

Figure 7:
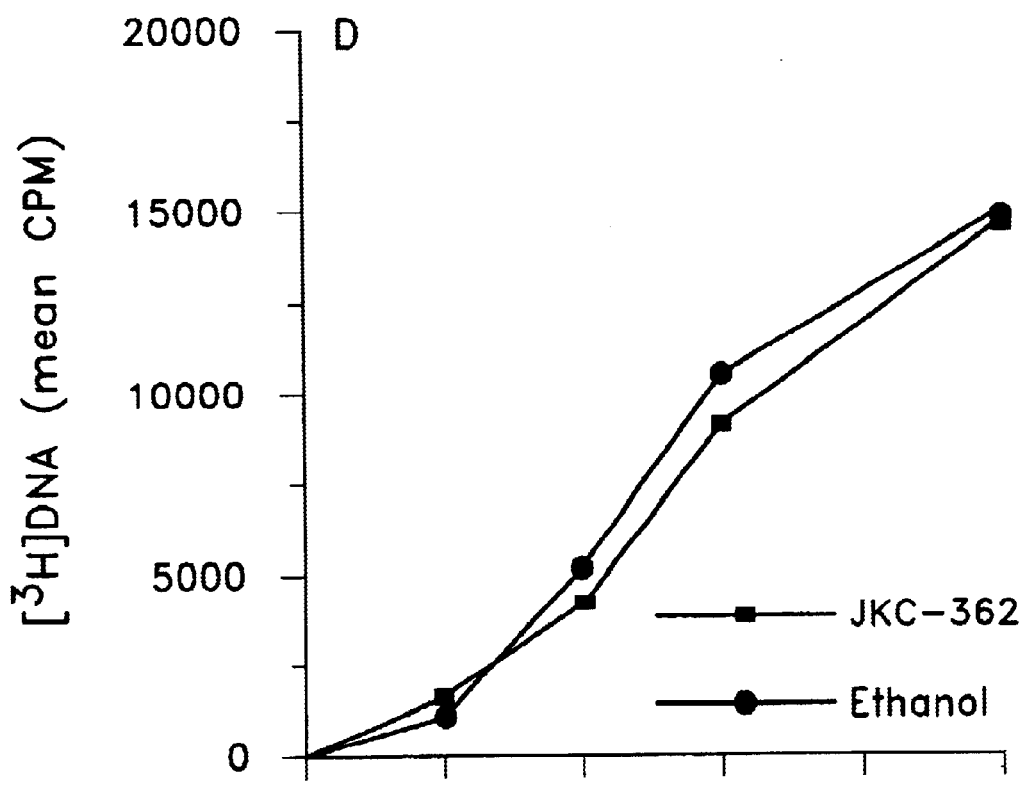
FIG. 7 shows a graph of the growth of human lung adenocarcinoma 201T cells in response to treatment with JKC-362.
Figure 8:
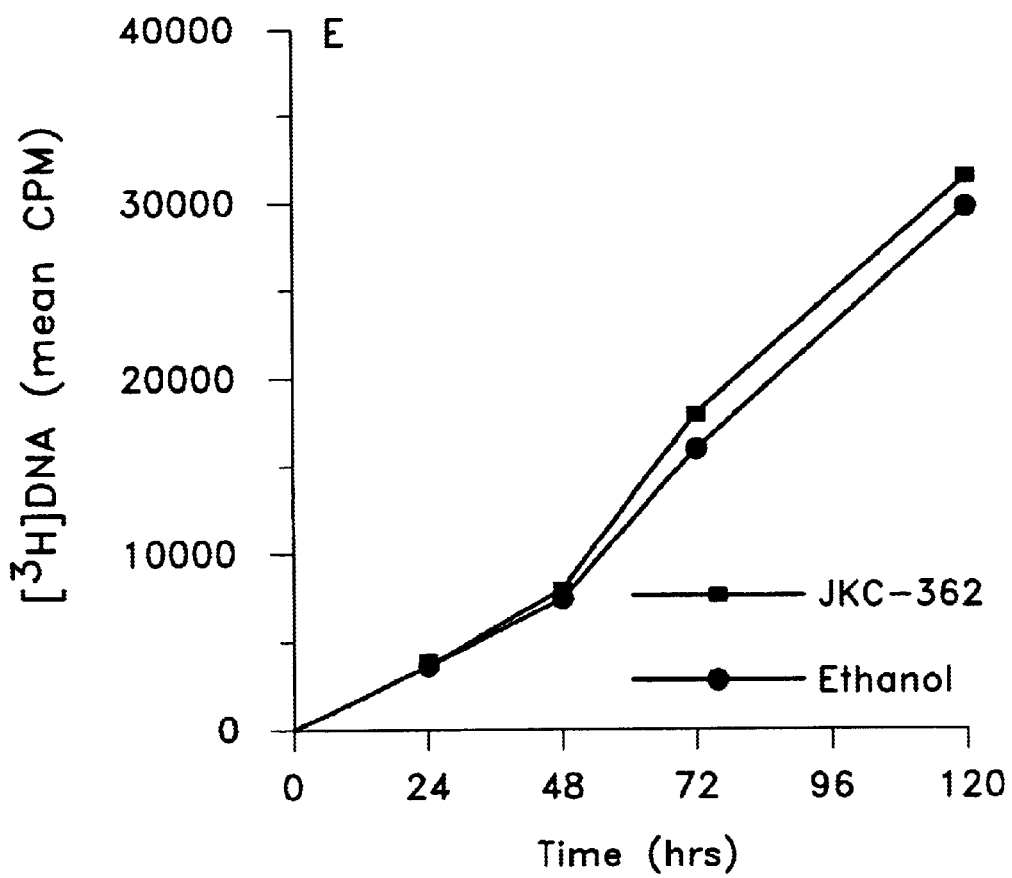
FIG. 8 shows a graph of the growth of PC-3cells in response to treatment with JKC-362.

Now referring to FIGS. 6-8, the human prostate carcinoma PC-3 and the human lung adenocarcinoma 201T were treated with increasing concentrations of the '362 peptide and '367 peptide in the presence of radioactive thymidine. As expected, no reduction in incorporation of radioactive thymidine was observed for PC-3 (FIG. 6A) or 201T (FIG. 6B) indicating no inhibition of tumor cell growth. These results are not surprising, because the '362 peptide should not have any effect on the cancer cells directly, but instead should act upon the growth of the cells that form new blood vessels. By inhibiting growth of these endothelial cells, blood vessels are inhibited from growing and nourishing growing tumors.

Human umbilical vein endothelial cells (HUVEC) were also grown in increasing concentrations of the '362 peptide or '367 peptide in the presence of radioactive thymidine. HUVEC cells are commonly used to test for angiogenic regulation because these cells respond to angiogenic inhibitors in a fashion similar to the cells in the human body that form new blood vessels. Surprisingly, the HUVEC did not demonstrate a reduced growth rate with exposure to increasing concentrations of the '362 peptide as shown in FIG. 6C or the '367 peptide. The same in-vitro treatment of HUVEC with endostatin protein resulted in a dramatic reduction in HUVEC growth. Research protocols designed to elucidate the reasons for this unexpected difference in response of HUVEC to endostatin protein and to '362 peptide are set out in the Research Plan, Phoenix Pharmaceuticals, Inc., 2438 Wyandotte Street, Mountain View, Calif. 94043, (1999) which is hereby incorporated by reference.

Figure 9:
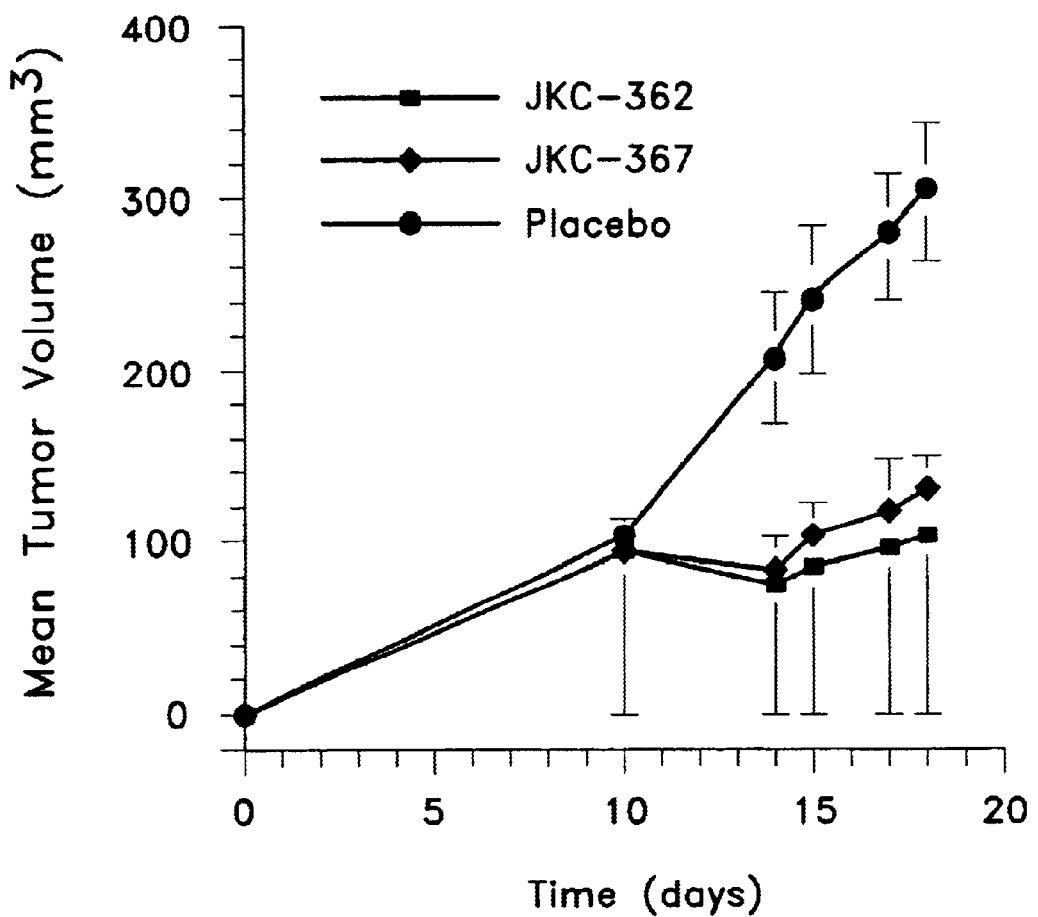
FIG. 9 shows tumor volume with respect to treatment with either JKC-362, JKC-367, or a placebo.

Referring to FIG. 9, which shows the results of treating human tumors established in nude mice with the '362 peptide. The human prostate cancer cell line PC-3 will grow well in athymic nude mice. These specialized mice have a severely impaired immune system which allows for the growth of human tumors without the fear of rejection. As such, athymic nude mice are used to test the effectiveness of new drug therapies as would be understood by those having skill in the art. PC-3 cells were implanted under the skin (subcutaneous) of 30 nude mice, and tumors were allowed to grow for 11 days until the tumor volume averaged about 100 mm$^3$ (the volume of tumors was calculated using ½π(W·L·H). The mice were then subdivided into three groups. Group 1 received daily injections of the '362 peptide at about 2.0 milligrams per kilogram body weight per day (mg/kg/day) for 14 days. Group 2 received daily injections of the '362 peptide at about 5.0 mg/kg/day for 14 days. Group 3 received daily injections of saline as a placebo (0.1 milliliter per day).

Figure 10:
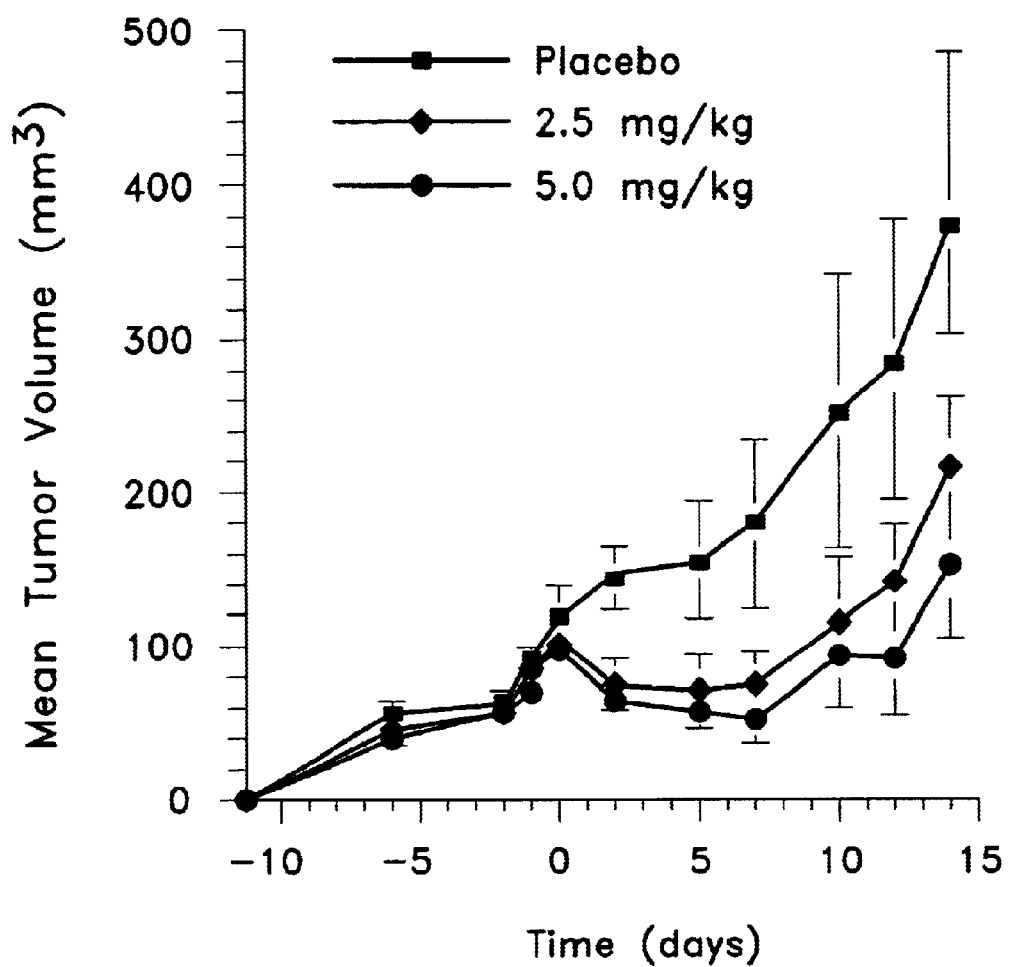
FIG. 10 shows tumor volume with respect to treatment with varying concentrations of JKC-362 or a placebo.

As shown by FIG. 10, there is a statistically significant reduction of tumor volume of tumors in treated mice versus the untreated mice (for 5.0 mg/kg/day, p<0.001; for 2.5 mg/kg/day, p<0.008, F test). Conventional doses of endostatin protein are about four times the maximum dose of '362 peptide of 5.0 mg/kg/day used in these experiments. See O'Reilly et al. (996) hereby incorporated by reference. More aggressive administration schedules are set out in the Research Plan, Phoenix Pharmaceuticals, Inc., hereby incorporated by reference. Similar to endostatin protein, neither the '367 peptide or the '362 peptide has induced acquired drug resistance to date.

It should be understood that a variety of changes may be made without departing form the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

In addition, each of the various elements of the invention and claims may also be achieved in a variety of manners. This disclosure should be understood to encompass each such variation, be it a variation of an embodiment of any composition, a method or process embodiment, or even merely a variation of any elements of these. Particularly, it should be understood that as the disclosed relates to elements of the invention, the words for each element may be expressed by equivalent apparatus terms or method terms— even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all action may be expressed as a means for taking that action or as an element which causes that action. Similarly, each physical element disclosed should be understood to encompass a disclosure of the action which that physical element facilitates. Regarding this last aspect, the disclosure of a "angiogenesis inhibitor" should be understood to encompass disclosure of the act of "inhibiting angiogenesis"—whether explicitly discussed or not—and, conversely, were there only disclosure of the act of "inhibiting angiogenesis", such a disclosure should be understood to encompass disclosure of a "angiogenesis inhibitor" and even a means for "inhibiting angiogenesis". Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the Information Disclosure Citation or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) the various embodiments of the purified polypeptide angiogenesis inhibitors or cell growth regulation system as herein disclosed and described, ii) the related methods disclosed and described, iii) similar, equivalent, and even implicit variations of each of these compounds and methods, iv) those alternative polypeptide compounds which accomplish each of the functions shown as disclosed and described, v) those alternative designs and methods which accomplish each of the functions shown as are implicit to accomplish that which is disclosed and described, vi) each feature, component, and step shown as separate and independent inventions, vii) the various combinations and permutations of each of the elements disclosed, viii) the resulting products produced by such systems or components, and ix) methods and apparatuses substantially as described hereinbefore and with reference to any of the accompanying examples.

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like.

I claim:

1. A purified polypeptide the amino acid sequence of which consists of SEQ ID NO: 1.

2. A purified polypeptide as described in claim 1, wherein said purified polypeptide has at least one conservative amino acid substitution.

3. A kit comprising at least one vessel containing a purified polypeptide the amino acid sequence of which consists of SEQ ID NO: 1.

* * * * *